United States Patent [19]

König

[11] 4,052,164

[45] Oct. 4, 1977

[54] APPARATUS FOR CENTRIFUGAL SEPARATION AND MEASUREMENT OF SAMPLES

[75] Inventor: Wolfgang König, Munich, Germany

[73] Assignee: Compur-Electronic Gesellschaft mit beschrankter Haftung, Munich, Germany

[21] Appl. No.: 732,218

[22] Filed: Oct. 14, 1976

[30] Foreign Application Priority Data

Nov. 26, 1972 Germany ............................ 2553044

[51] Int. Cl.² ......................... G01N 33/16; B04B 5/00

[52] U.S. Cl. .......................................... 23/259; 233/26

[58] Field of Search ..................... 23/259, 292; 233/26

[56] References Cited

U.S. PATENT DOCUMENTS

| | | | |
|---|---|---|---|
| 2,507,309 | 5/1950 | Larsson | 233/26 |
| 3,679,367 | 7/1972 | Negersmith et al. | 23/259 |
| 3,720,368 | 3/1973 | Allen | 233/26 |
| 3,748,101 | 7/1973 | Jones et al. | 23/259 |
| 3,891,140 | 6/1975 | Ayres | 233/26 |

*Primary Examiner*—R.E. Serwin
*Attorney, Agent, or Firm*—Stonebraker, Shepard & Stephens

[57] ABSTRACT

A rotor, adapted for rotation at high speeds, has symmetrically arranged radial channels for receiving tubular containers of material to be evaluated such for example as samples of blood. The outer end of each radially extending container filled with the sample to be evaluated is placed against a resilient abutment at the rim of the rotor, and the inner end of the container is placed in a receiving groove in a clamping member having limited axial movement relative to the axis of rotation of the rotor. The length of each sample container is such that it fits fairly snugly between the abutment and the clamping member when at a slight inclination to the plane of rotation of the rotor (that is, a plane perpendicular to the axis of rotation) when the clamping member is in a loading position. When the clamping member is then moved axially to its locking position, the sample container is swung through the plane of rotation to a slight angle on the opposite side thereof from the loading position, meanwhile compressing the resilient abutment at the outer end of the container by a toggle action. This holds the container firmly and safely for rotation at high speed, to separate the components of the contents of the container by centrifugal action. The results of the separation may be read on a numerical scale marked on the rotor alongside each container.

7 Claims, 3 Drawing Figures

Fig. 3
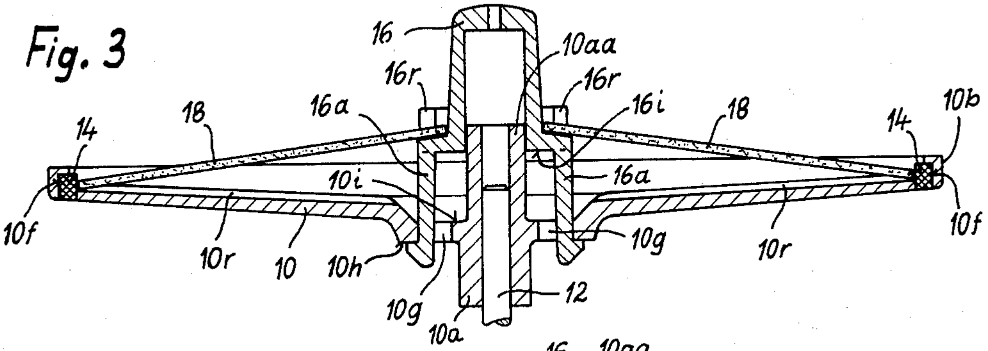
Fig. 1
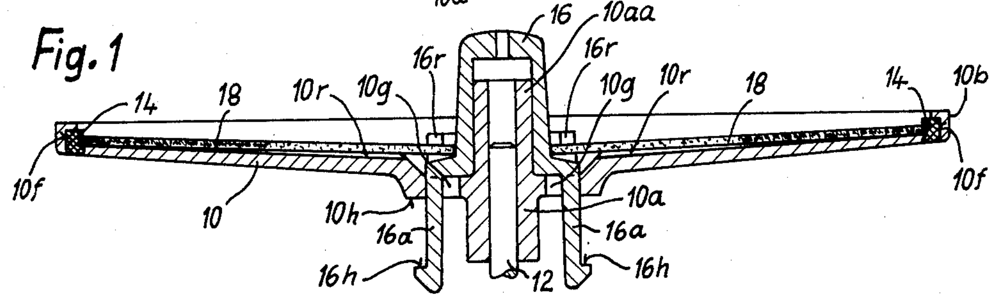
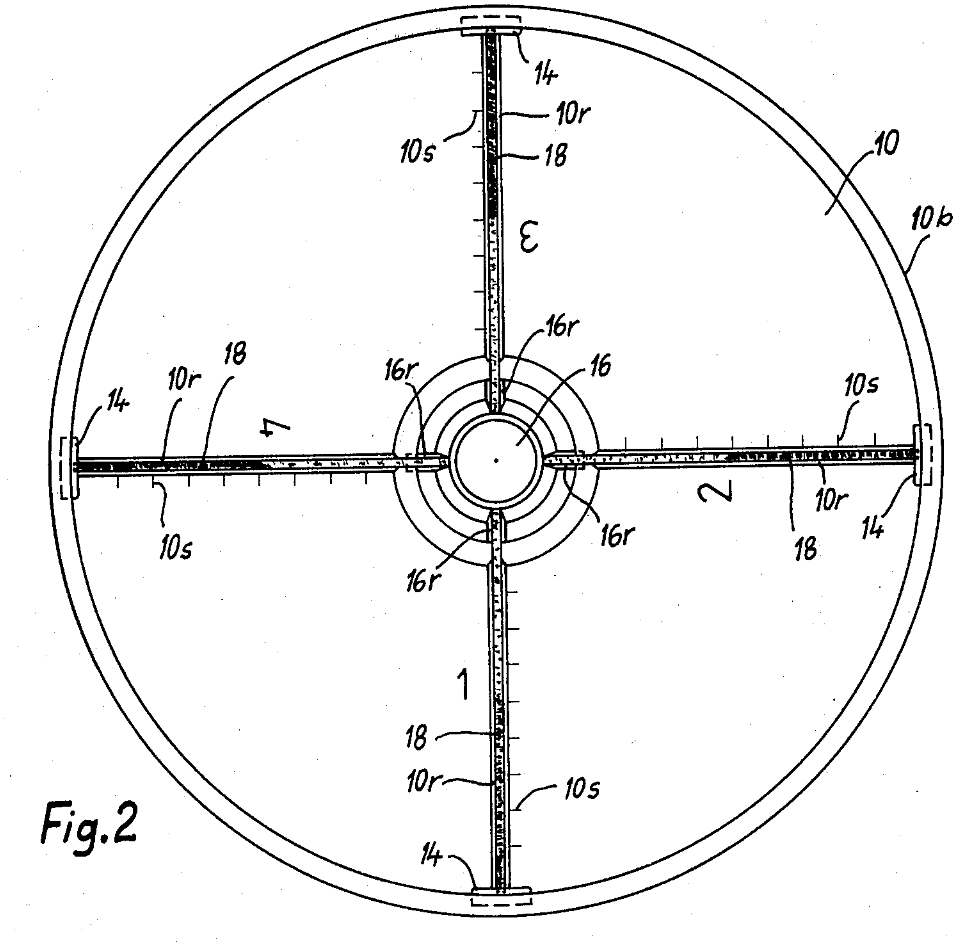
Fig. 2

APPARATUS FOR CENTRIFUGAL SEPARATION AND MEASUREMENT OF SAMPLES

BACKGROUND OF THE INVENTION

This invention relates to the evaluation or testing of various substances placed in small cylindrical containers, which may be regarded as one form of cuvet. Such containers are well known in the medical and biological field, and are frequently made of glass or plastic tubes of such small diameter that a liquid to be tested is drawn into the tube by capillary action. A typical material frequently tested is blood. The evaluation tests to be made on blood or other substances frequently include a separation of the ingredients or components of the liquid being tested, by subjecting the liquid to centrifugal force, and subsequent measurement of the separated components.

An object of the present invention is to provide a relatively simple structure which can be used without difficulty and rapidly for clamping the containers in the appliance, and which also guarantees a firm sealing of the containers in the rotor even at high speeds of rotation.

This object is well fulfilled by apparatus according to the invention, a preferred embodiment of which is herein disclosed as an example.

BRIEF DESCRIPTION OF THE DRAWINGS

FIG. 1 is a diametrical section through the rotor in accordance with a preferred embodiment of the invention, and associated clamping parts in the clamping position;

FIG. 2 is a plan of the parts shown in FIG. 1; and

FIG. 3 is a view similar to FIG. 1, with the clamping parts in unclamped or loading and unloading position.

DESCRIPTION OF THE PREFERRED EMBODIMENT

There is a rotor 10 in the form of a circular plate of slightly dished shape as seen in diametrical axial section. The hub portion 10*a* of the rotor is firmly mounted on a shaft 12 having suitable driving means for rotating it at high speed. For example, the shaft 12 may be the shaft of a conventional centrifuge, the details of which are well known and not illustrated, capable of being rotated at high speed by an electric motor.

On the upper surface of the rotor plate are any desired number of symmetrically arranged radially extending grooves 10*r* for receiving tubular containers or cuvets containing material to be evaluated or tested. Four such grooves are here illustrated, but more or less may be used. The upper surface of the rotor disk, containing these grooves, is dished or slightly inclined downwardly from the rim toward the center, as readily seen in FIG. 1. The outer rim 10*b* of the rotor has an upwardly extending marginal flange. In this flange, opposite the outer end of each of the radial grooves 10*r*, is an opening 10*f* having inserted therein a buffer or abutment member 14 of resilient material with good sealing properties, such as natural or artificial rubber.

The hub portion 10*a* of the rotor has an upwardly extending tubular portion 10*a*. A hollow clamping member 16 fits snugly but slidably on this hub extension 10*aa*, for limited upward and downward movement thereon. Formed in the rim of the clamping member 16 are open reception slots 16*r* in radial alignment with the reception slots 10*r* of the rotor. The clamping member has two diametrically opposite radially extending arms 16*a* extending down as illustrated through two openings 10*g* in the rotor 10, the lower ends of these arms having outwardly extending lugs or projections the upper faces 16*h* of which cooperate with the lower face 10*h* of the rotor to limit the upward motion of the clamping member 16 relative to the rotor. An internal shoulder 16*i* of the clamping member overlies an upper face portion 10*i* of the rotor to limit downward motion of the clamping member 16 relative to the rotor. Thus these respective abutment surfaces 10*h*, 16*h* and 10*i*, 16*i*, define the two axial operating positions of the clamping element relative to the rotor, namely, the clamped position illustrated in FIG. 1 and the unclamped loading or unloading position illustrated in FIG. 3. The openings 10*g* and the arms 16*a* are so dimensioned and formed that there is a positive coupling for driving the clamping element 16 during the rotary movements of the rotor; in other words, the clamping member 16 cannot turn relative to the rotor, although it may move axially relative to the rotor, within the limits indicated.

Each of the radial grooves 10*r* for receiving the sample container has its own individual identifying numeral, as shown in FIG. 2 at "1", "2", "3", and "4". In addition, a graduated reading scale 10*s* is marked alongside each groove, the graduations preferably being marked with numerals (not shown).

This apparatus is intended for use with transparent tubular containers or cuvets of capillary size and all of a certain uniform length. The technician or other user of the device extracts the sample, for example blood, filling the capillary tube therewith. The filled cuvets are then placed on the rotor 10, one at each groove 10*r*, while the clamping member 16 is in its upper or unclamped position shown in FIG. 3, the cuvets being illustrated at 18. In each case, the outer end of the cuvet rests agains the resilient abutment or sealing member 14 at the outer end of its particular groove, and the inner end of the cuvet rests in its particular groove 16*r* of the clamping member.

When all cuvets have been placed in their proper radial positions, the user presses downwardly on the clamping member 16, moving it down from the position shown in FIG. 3 to the position shown in FIG. 1. In the initial position, the cuvets 18 were slightly inclined upwardly from the rim toward the center, in other words being dished upwardly from the plane of rotation of the rim of the rotor. As the clamping member 16 moves downwardly, the inner ends of the cuvets are displaced downwardly until, for a moment, they lie in the plane of rotation of the rim of the rotor, and are then further displaced downwardly to a position with the inner ends of the cuvets slightly below the plane of rotation as illustrated in FIG. 1, with each cuvet fully seated in its individual radial groove 10*r*. During this downward motion, the cuvets have been forced slightly outwardly in a radial direction due to the toggle effect, but this has been possible without breaking the cuvets on account of the resilient or compressible nature of the sealing abutments 14, which have been able to compress slightly upon moving the clamping member down from the FIG. 3 position to the FIG. 1 position. In the clamped position, the outer ends of all of the cuvets are tightly sealed against their respective resilient buffers or abutments 14.

Thereupon the driving motor of the centrifuge is switched on, and the rotor 10 is rotated at high speed, the clamped sample containers or cuvets 18 rotating bodily therewith. After a predetermined interval of rotation, depending upon the type of sample, for example after 3 minutes, the drive is switched off, preferably by automatic timing mechanism of known form. The solid components of the sample being evaluated which have been thrown radially outwardly within each cuvet by centrifugal force during rotation, and the lighter components thereof which collect at the inner end of each cuvet, can be readily seen and distinguished through the transparent walls of the cuvet. For example, when the sample being evaluated is blood, the solid blood components are thrown to the outer end and the lighter blood serum is collected at the inner end of each capillary tube 18, and can distinctly be seen separated. The line of separation serves as a marker which permits the reading of a measured value on the graduated scale 10*s* for each of the various capillary tubes "1", "2", "3", and "4", that is to say, for example, the haematocritical value, or proportion of the corpuscular elements, such as erythrocytes and leucocytes in percentages of the total blood.

When the desired readings have been taken and recorded, the clamping member 16 is pulled upwardly, from the position of FIG. 1 to the position of FIG. 3. The cuvets or sample containers 18, now unclamped and loose again, are removed, and other sample containers with other material to be evaluated are placed on the rotor when the next evaluation is to be made.

The rotor 10 and the clamping member 16 can advantageously be made as injection moldings, thus providing for favorable and inexpensive mass production of the clamping assembly.

It may be noted that when moving from the unclamped position of FIG. 3 to the clamped position of FIG. 1, the inner ends of the cuvets 18 pass from one side to the other side of the plane of their outer ends, or in other words they pass through what may be described as a "dead center" position. It is not necessary to provide any latch for holding the clamping member 16 in its clamped position, because the endwise compressive force on the cuvets, due to the compression of the resilient members 14, has a component tending to move the clamping member downwardly because of the dished or downwardly slanting position of the cuvets. Yet the downward inclination of the containers 18 in the clamped position is only a slight inclination, much less than the upward inclination in the unclamped position, thus insuring that the containers are tightly compressed between the non-resilient surface of the clamping member at their inner ends and the respective resilient sealing abutments 14 at their outer ends.

The present invention thus provides apparatus of simple, sturdy, and inexpensive character, easily and quickly loaded with the samples to be evaluated or tested, with provision for reading the results of the centrifugal test while the test samples are still in the apparatus, and capable of being easily and quickly unloaded to remove the samples already tested and to make the apparatus ready for receipt of fresh samples.

What is claimed is:

1. Apparatus for centrifugal separation of test samples in containers of tubular form open at both ends, said apparatus comprising a rotor of plate-like form having a plurality of radially extending recesses each being adapted to accommodate one of said tubular containers, resilient abutment means on said rotor at the outer end of each recess in position to serve as an abutment for the outer end of a tubular container laid in such recess, clamping means mounted centrally on said rotor and movable axially from a loading position to a clamping position, said clamping means forming a movable abutment for the inner ends of the tubular containers, said axial movement of said clamping means carrying the inner ends of the tubular containers from a position on one side of a transverse plane perpendicular to the axis of rotation of said rotor and containing the outer ends of said containers to a position on the opposite side of said plane, and said axial movement of said clamping means serving to displace a tubular container radially outwardly into tight sealing and clamping engagement with said resilient abutment means.

2. Apparatus as defined in claim 1, wherein the tubular containers, when placed on said rotor with said clamping means in loading position, are inclined in one direction relative to a plane perpendicular to the axis of rotation of said rotor, and the axial movement of said clamping means to clamping position shifts the inner ends of said containers to incline them in an opposition direction relative to said plane.

3. Apparatus as defined in claim 2, wherein the degree of inclination of said containers when said clamping means is in loading position is substantially greater than the degree of inclination thereof in the opposite direction when said clamping means is in clamping position.

4. Apparatus as defined in claim 1, wherein said axial movement of said clamping means from loading position to clamping position moves said inner ends axially of the axis of rotation of said rotor from an inclined position to and slightly beyond a straight position to exert radially outward force on said containers in the manner of force exerted by straightening a toggle.

5. Apparatus as defined in claim 1, further comprising means forming a positive connection in a rotational direction between said rotor and said clamping means, so that when said rotor is rotated, said clamping means is positively entrained to rotate with it.

6. Apparatus as defined in claim 1, further comprising cooperating abutment faces on said rotor and said clamping means to limit axial movement of said clamping means.

7. Apparatus as defined in claim 1, further comprising a graduated scale on said rotor beside each of said radial recesses, for measuring values resulting from centrifugal action on the contents of tubular containers clamped to and rotated with said rotor.

* * * * *

UNITED STATES PATENT AND TRADEMARK OFFICE

CERTIFICATE OF CORRECTION

PATENT NO. : 4,052,164

DATED : October 4, 1977

INVENTOR(S) : Wolfgang König

It is certified that error appears in the above-identified patent and that said Letters Patent are hereby corrected as shown below:

On the cover sheet, item [30], Foreign Application Priority Data, for "Nov. 26, 1972" read --Nov. 26, 1975--.

Signed and Sealed this

*Twenty-seventh* Day of *December 1977*

[SEAL]

*Attest:*

RUTH C. MASON
*Attesting Officer*

LUTRELLE F. PARKER
*Acting Commissioner of Patents and Trademarks*